(12) United States Patent
Chadwick (10) Patent No.: US 6,675,112 B1
(45) Date of Patent: Jan. 6, 2004

(54) CURE MONITORING (75) Inventor: Duncan Chadwick, Stoke-on-Trent (GB)

(73) Assignee: The Manchester Metropolitan University, Manchester (GB)

( * ) Notice: Subject to any disclaimer, the term of this patent is extended or adjusted under 35 U.S.C. 154(b) by 0 days.

(21) Appl. No.: 09/857,420

(22) PCT Filed: Dec. 6, 1999

(86) PCT No.: PCT/GB99/04114

§ 371 (c)(1),
(2), (4) Date: Nov. 30, 2001

(87) PCT Pub. No.: WO00/34770

PCT Pub. Date: Jun. 15, 2000

(30) Foreign Application Priority Data

Dec. 4, 1998 (GB) ............................................ 9826787

(51) Int. Cl.⁷ ............................................... G01M 1/00
(52) U.S. Cl. ............................ 702/56; 73/54.41; 73/573
(58) Field of Search ........................... 702/54; 73/54.41, 73/573, 579, 582, 599, 457; 324/71.1

(56) References Cited

U.S. PATENT DOCUMENTS

| | | |
|---|---|---|
| 4,455,268 A | 6/1984 | Hinrichs ..................... 264/407 |
| 4,758,803 A | 7/1988 | Thomas, III ................ 324/714 |
| 4,862,384 A | 8/1989 | Bujard ......................... 702/54 |
| 5,505,090 A | 4/1996 | Webster ....................... 73/657 |
| 5,533,399 A | 7/1996 | Gibson ......................... 73/579 |
| 6,029,520 A | * 2/2000 | Beall et al. ................... 73/579 |

\* cited by examiner

Primary Examiner—Kamini Shah
(74) Attorney, Agent, or Firm—Nixon & Vanderhye PC (57) ABSTRACT

A method and apparatus for monitoring the progress of the solidification of a solidifying material involves using a transmitter to transmit a relatively low frequency compression wave to the solidifying material. A receiver is provided for detecting the resonant compression wave vibrations induced in the solidifying material, and the detected wave vibrations are analyzed to obtain an indication of the progress of solidification.

48 Claims, 5 Drawing Sheets

CURE MONITORING

BACKGROUND OF THE INVENTION

This invention relates to the monitoring of solidification of plastics resins, and in particular relates to monitoring the curing of adhesively bonded or sealed joints, monitoring the cure of thermosetting resins and monitoring the cure of composite materials comprising plastics resins.

As a thermosetting polymer cures, its temperature generally rises and the viscosity falls until the gel point is reached, after which the viscosity rises rapidly until solidification is complete, whether this is in a composite structure or an adhesive bond, the way in which components are handled during this time is critical. For example in the case of an adhesive bond, if the components are brought together under pressure too early, the low viscosity resin will be forced from the bond, producing less than optimum bond thickness and large amounts of spew. If the components are forced together too late the adhesive will have begun to gel and a network will have begun to form, thus the molecular structure of the adhesive will be disturbed.

Similar situations exist in composite manufacture e.g. pressure moulding of composite panels in stop-less or picture frame moulds. In both types of application, once the solid polymer structure begins to form the components must be held exactly in place. Once sufficient strength has built up (the 'green' strength has been reached) the completed structure may be removed from the mould or jig and curing completed in a second oven. In order to optimise production time and quality it is important to know when i) the gel point is reached,
ii) green strength has developed, and
iii) cure is complete.

Hitherto, methods of determining state of cure of plastics resins have been limited to destructive examination and testing or off-line techniques. Ultrasonics, Radiography and low frequency techniques are known in the non-destructive testing (NDT) of adhesive bonds and composite materials. However current low frequency techniques are limited to the detection of disbonds etc., in a polymer after curing. The usefulness of radiography is severely limited by the limited range of adherend, which may be used, and by the orientation of the defects being sought.

Ultrasonic techniques are limited by both the type of adherend and adhesive. In particular, if either adherend or adhesive is significantly acoustically absorbing, then it is not possible to apply such techniques.

U.S. Pat. No. 4,862,484 is concerned with the measurement of the dynamic viscosity of a viscous medium using an acoustic transducer in the temperature and pressure environment of the medium and spaced therefrom. The specification discloses the use of an ultrasonic frequency and the viscosity of the fluid is calculated using the shift between the first and second resonant frequencies and the difference between first and second band widths. Such a system is limited, effectively, to measuring frequency in a substantially liquid material and does not permit the monitoring of the cure of a material after effective solidification.

U.S. Pat. No. 4,758,803 relates to the detection of ultrasonic properties of fibre reinforced plastics during the curing process. Such a system has only limited application since ultrasound is absorbed by some polymers and reinforcers and is not effective in the monitoring of post solidification curing.

U.S. Pat. No. 4,455,268 is concerned with an automatic system for controlling the curing process of structures formed of fibre reinforced composite materials in an autoclave. The specification is concerned with the measurement of viscosity data through measurements of attenuation of ultrasonic waves in the composite material of the structure. This specification teaches that attenuation is directly related to the viscosity of the structure which is then compared with a "model" profile.

None of these techniques are able to detect poor cohesion or adhesion in-situ and do not permit effective continued monitoring after solidification.

The foregoing techniques may be used in the non-destructive testing (NDT). of composite materials, however significant problems exist. The use of radiography is limited because composite materials, particularly carbon fibre reinforced composites, are weak absorbers of. X-rays. Thus it is difficult to produce high contrast images. Ultrasonic techniques can be used but problems can occur due to scattering produced from filler particles and fibre reinforcement.

Methods currently used to monitor cure include quantitative. (wet) analysis, Fourier transform infrared, Raman, near infrared, nuclear magnetic and electron spin resonance spectroscopy, DSC, DPC, torsional braid analysis, dynamic mechanical thermal analysis, dielectric techniques, Theological methods and ultrasonic techniques.

Quantitative analysis. requires the removal of a sample of the resin to determine the content of an active group involved in the cross-linking reaction, for example epoxy or hydroxyl in the case of epoxy resins. Although the technique may be used to detect off-stoichiometric effects in a cured resin it is not feasible to use it as a cure monitoring technique. Spectroscope techniques provide information regarding the state of the chemical reaction and are useful as research tools. However many such techniques require access to the surface of the curing polymer which is clearly difficult in many industrial applications e.g. large composite structures and adhesive bonds.

This problem can be overcome to some extent by using optical fibres, however these must then remain in the cured structure and may potentially act as crack initiators. This is obviously undesirable, particularly in critical structural applications. Spectroscopic techniques require the polymer to be placed in a particular environment e.g. Nuclear Magnetic Resonance where the sample is placed in a strong fixed magnetic field. Again, this is not feasible in many industrial applications.

Dynamic mechanical thermal analysis, DSC and DPC are again useful research laboratory tools. However the techniques also rely upon removing a sample of curing polymer and placing it in a controlled environment within the instrument, thus in-situ measurements are not possible. Dielectric techniques measure changes in permittivity that occur during the polymerisation process as a result of changes in the concentration of functional groups. Such methods involve placing electrodes in the curing polymer, these remain in the polymer once it has cured and may act as crack initiators.

Torsional braid analysis involves the impregnation of a glass fibre braid with uncured liquid monomer. This braid is then subjected to a sinusoidal torsional force and complex modulus determined. Again this involves leaving a foreign body in the cured resin and whilst this may be acceptable in composite manufacture where crack propagation may not be critical, it would not be acceptable in general adhesive bonding.

A number of Theological techniques are available which essentially follow the physical properties of the resin until the point when it becomes solid. These are laboratory techniques and not suited to making in-situ measurements.

Finally, ultrasonic techniques do potentially allow the NDT/NDE of a curing polymer in-situ. However, like the ultrasonic flaw detection techniques, they are not suited to adherend/adhesive combinations that are highly acoustically absorbing.

Accordingly there is a need for a non-destructive method for the monitoring of the progress of curing in plastics resin materials or structures comprising those materials.

There are a number of low frequency tests already in the market place which are used to detect dis-bonds and delaminations in formed composites. Many of these are based on the 'coin tap' test. In its simplest form the 'coin tap' test involves tapping the component under test with a metallic striker. Defective areas will sound 'dead' due to absorption at the defect site. For example, tapping a good railway wheel will produce a clear sustained ring, whilst a cracked wheel produces a short 'dead' ring. Essentially the fundamental frequency of the defective wheel is lower and more heavily damped, thus producing a ring of lower frequency and shorter duration. The flaw causes a local increase in structural flexibility and hence a change in the nature of the impact. The impact over a good area is more intense and of a shorter duration. This is the principle behind the Tapometer™ (trade name) produced by Rolls-Royce Mateval Ltd which compares the frequency response of a measured pulse with that of a structure which is known to be good.

The Shurtronics Harmonic Bond Tester (trade name) looks for defects in a similar way. This works on the principle that the area above a dis-bond or delamination may be regarded as a plate which is restrained around its edges. The response over a defect is of greater amplitude and of longer duration than that of a over a good area. A microphone is used to monitor the vibration produced in the structure.

SUMMARY OF THE INVENTION

The present invention stems from the discovery that, surprisingly, low frequency (i.e. below ultrasonic frequencies) compression wave analysis may be used to characterise the progression of solidification of plastics resins, and in particular thermosetting plastics.

There is nothing in the prior art known to the inventor to suggest that such techniques may be used to monitor the curing of unset plastics resin material, bonds or structures. All the prior art tests involve low frequency testing carried out on solidified materials or structures. That such tests should be effective on flowable or gelling solidifying material is counter-intuitive because of the rapid attenuation of compression waves in non-solids.

The present applicants have found surprisingly, that as cure proceeds the frequency of the induced resonance increases, reflecting the decrease in the flexibility of the structure. The signal amplitude generally decreaes to a minimum part way through the cure cycle before increasing again. These results have been corroborated with experiments carried out on bulk specimens of epoxy resin using ultrasound and low resolution pulsed NMR.

In a particular aspect of the invention the material is a thermosetting polymer, such as epoxy resin. In this case the method can be used to monitor the onset and various stages of curing up to the attainment of green strength in the resin. The technique has also been found effective for monitoring the progress of solidification in thermoplastic resins.

The method finds particular application with regard to the monitoring of the cure of thermoset materials, or thermoset material-containing structures or composites.

In one aspect of the invention the frequency of a vibrational mode is monitored as a function of time.

In another aspect of the invention the amplitude of the mode is monitored as a function of time. In yet another aspect of the invention both frequency and amplitude of a vibrational mode are measured as a function of time.

By correlating the output signal behaviour with a database of known behaviour for individual materials or structures particular physical, mechanical or chemical properties of the resins may be obtained sampled or monitored over a time period. This can be used to provide data useful for indicating when to apply pressure to bonds or composite laminates, or when pressure may be released or products released from moulds. The skilled person will be able to make wide use of the present invention in the field of polymer processing.

The method involves inducing a resonant ring in the structure under test and then observing the characteristics of that ring. This allows detailed monitoring of the cure of thermosetting materials in-situ in structures or moulds.

In one aspect of the present invention, the compression wave transmitter is a piezo-electric transducer. The compression waves may be transmitted through a metal sheet to the plastics material under test. Typically, the metal sheet is steel.

The receiver may be spaced from said transmitter and located on said metal sheet. In one aspect of the invention, the receiver may be a piezo-electric transducer, which converts compression wave signals induced by the transmitter into an electric signal.

The signal obtained by the receiver may be passed to signal analyser means whereby the output from the receiver is analysed to provide information about the progress of the cure or solidification. In another aspect, the signal analyser may also includes database means comprising data relating to the sound transmission characterisitics of solidifying/curing materials, and in that monitoring comprises comparing changes in the received signal with corresponding data in said database means.

The signal analyser means associated with the receiver is adapted to monitor an increase in frequency of the induced resonance which reflects a decrease in the flexibility of the structure and a signal amplitude which generally decreases to a minimum part way through the cure cycle before increasing again as the solidification process proceeds to completion.

In one embodiment of the invention, the transmitter may be driven by a pulser. The pulser may also be connected to the first channel of a digital storage adapter a second channel of which is connected to the receiver; a first output from the adapter is connected to an oscilloscope to provide a visual signal indication and a second output form the adapter is connected to a computer the arrangement being such that the computer stores and processes signal data to provide information about the curing process.

In another embodiment of the invention a single transducer may act as both a receiver and transmitter. The transmitter may be excited with a square wave of 20 to 40 Hz.

This method is capable of characterising a number of stages of curing and may be calibrated to provide a wide range of physical property information. For example the technique may be used to determine the gel point of thermosetting materials. The technique may also be used to determine the green, strength of thermosetting materials.

BRIEF DESCRIPTION OF THE DRAWINGS

Following is a description by way of example only and with reference to the drawings of methods of putting the present invention into effect.

In the drawings.

DETAILED DESCRIPTION OF THE INVENTION

Figure 1A:
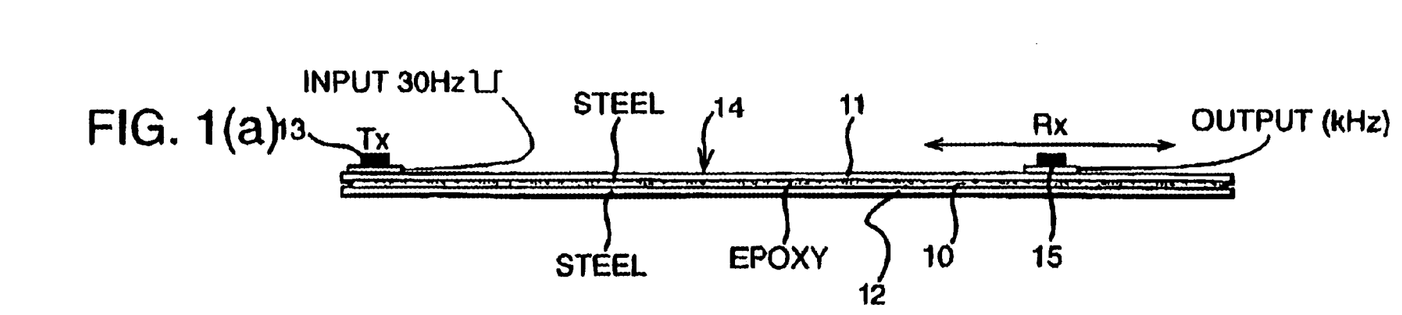
FIGS. 1A and 1B show apparatus for monitoring the curing of an epoxy resin layer between two steel plates.
Figure 1B:
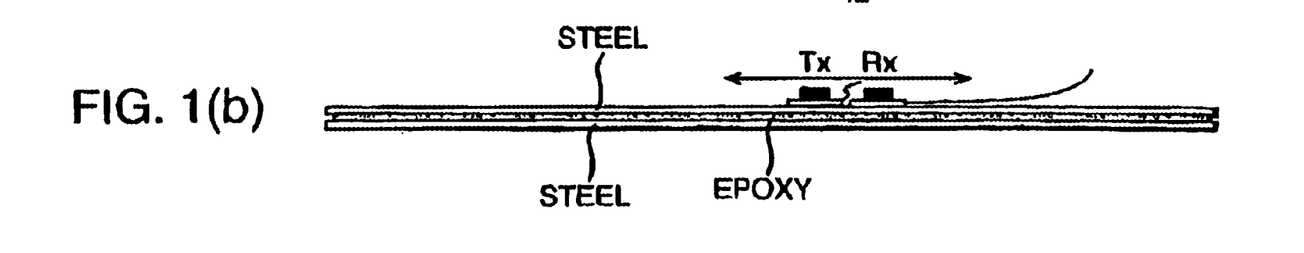

In FIG. 1A apparatus is shown for studying the curing of an epoxy resin bond 10 between two steel sheets 11, 12. A compression wave transmitter 13 is a piezo-electric transducer. The transmitter is juxtaposed an exposed surface 14 of the upper steel sheet 11. Compression waves are transmitted through the steel sheet to the epoxy layer on the lower sheet 12. Spaced apart from the transmitter is a receiver 15. The receiver is also in contact with the upper surface of the top sheet 11. The receiver is a piezo-electric transducer, but converts compression wave signals induced by the transmitter into an electric signal which may be analysed to provide information about the progress of the epoxy cure. An alternative configuration is shown in FIG. 1B, in which the components are identical but the receiver is located adjacent the transmitter.

Figure 2:
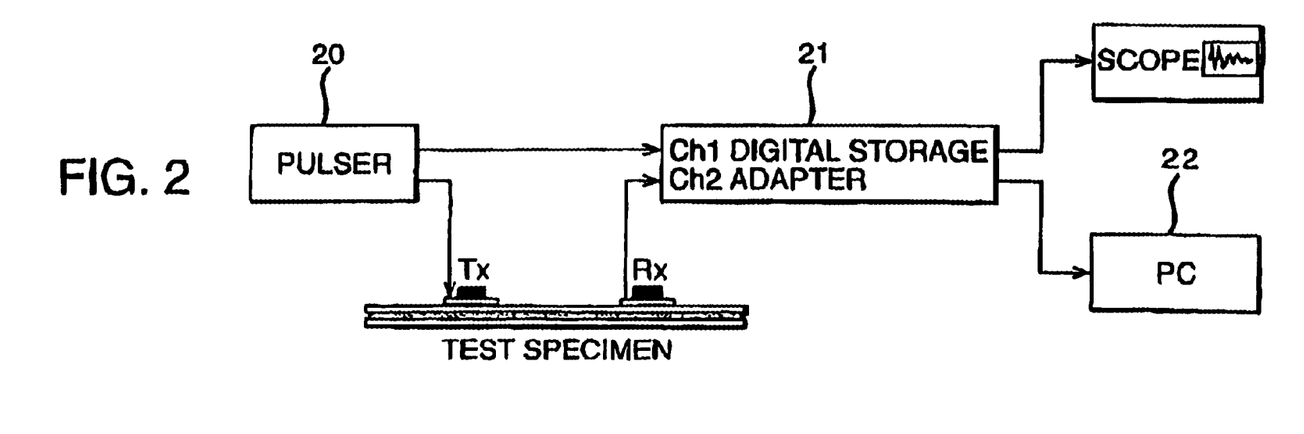
FIG. 2 shows a schematic view of apparatus for carrying out an embodiment of the invention.

The complete apparatus is shown schematically in FIG. 2, in which components already described are given corresponding numbering. The transmitter is driven by a pulser 20. The pulser is also connected to the first channel of a digital storage adapter 21. A second channel of the adapter is connected to the receiver. A first output from the adapter 21 is connected to an oscilloscope to provide a visual signal indication. A second output is connected to a personal computer 22. The personal computer stores and processes signal data to provide information about the curing process.

There are a number of variations to the apparatus that could be used to achieve the same result. For instance, given suitable signal processing equipment, a single transducer could act as both a receiver and transmitter. Several other types of known transducers could be used both to create and detect the induced resonance.

When the subject structure is tapped by the transmitter the characteristics of the impact were dependent upon the local mechanical compliance of the structure. As the physical properties of the resin change as a function of time during cure, then so do the characteristics of the impact and the amplitude and frequency of the induced vibration.

In one experiment, the transmitter 13 was excited with a square wave of 30 Hz. This induced frequencies of the major structural modes of vibration which were then received by the second transducer 15. These modes were found to have a frequency in the order of kHz., and the amplitude and frequency of the induced vibration as a function of cure time was monitored to provide the graph shown as FIG. 3.

Figure 8:
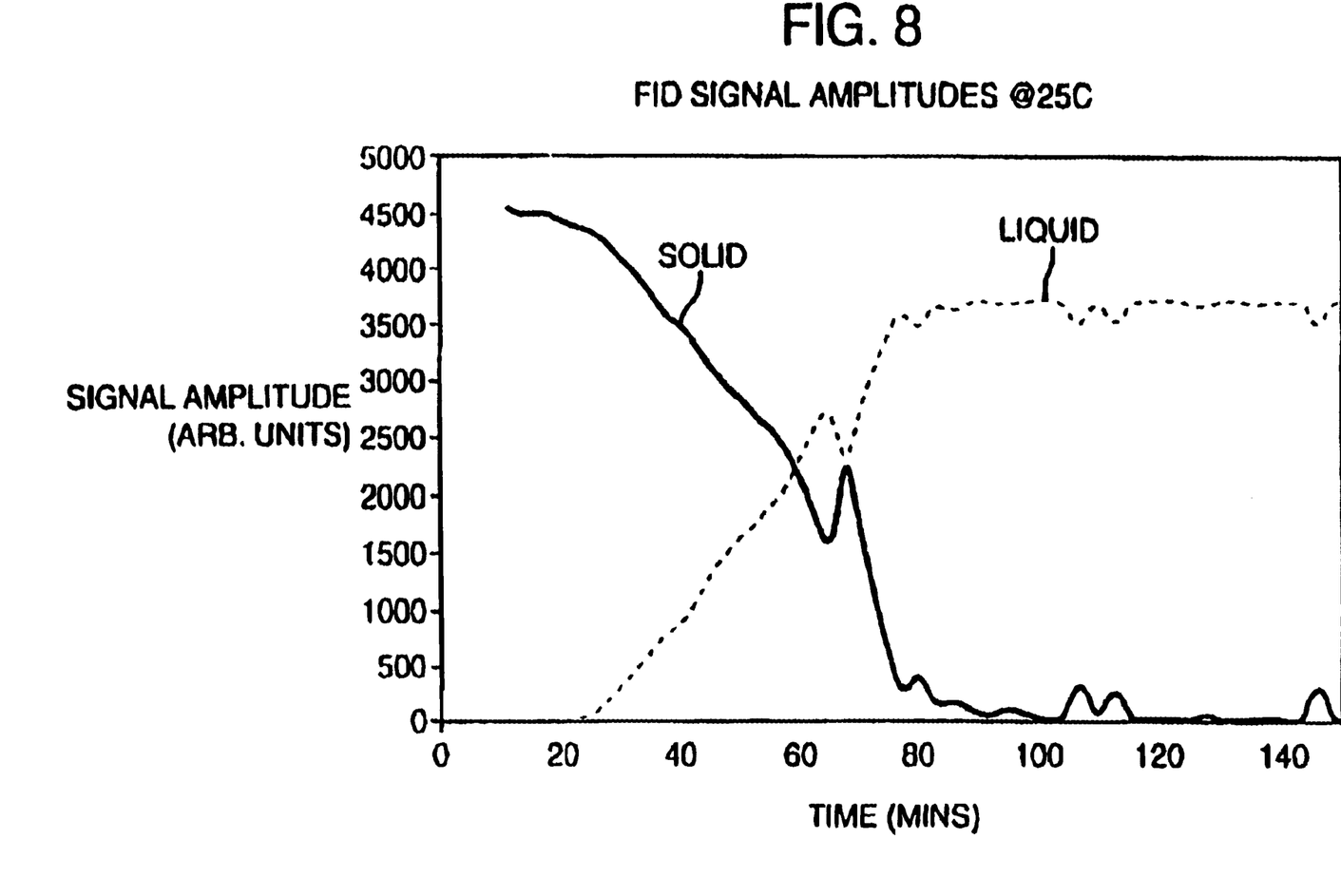
FIG. 8 is a comparative low resolution pulsed NMR graph of solid and liquid signal amplitudes as a function of cure time.

It can be seen that, generally, as cure proceeds the frequency of the induced resonance increases, reflecting the decrease in the flexibility of the structure. The signal amplitude generally decreases to a minimum part way through the cure cycle before increasing again. These results have been corroborated with experiments carried out on bulk specimens of epoxy resin using ultrasound (FIGS. 4,5,6 and 7) and low resolution pulsed NMR (FIG. 8).

The low frequency vibration technique was able to resolve four distinct stages in the cure process, which may be interpreted in the following way.

Figure 3:
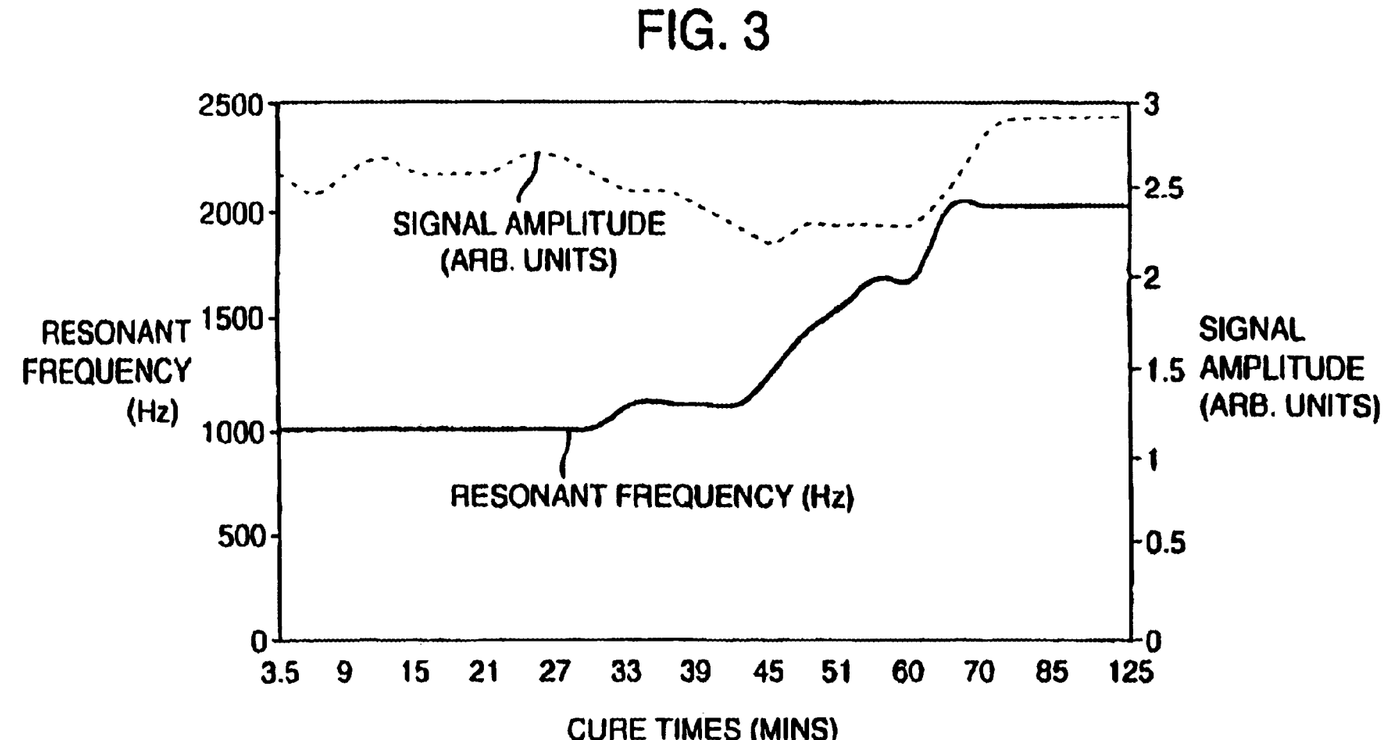
FIG. 3 is a graph showing the amplitude and frequency of induced vibrations in epoxy resin as a function of cure time.
Figure 4:
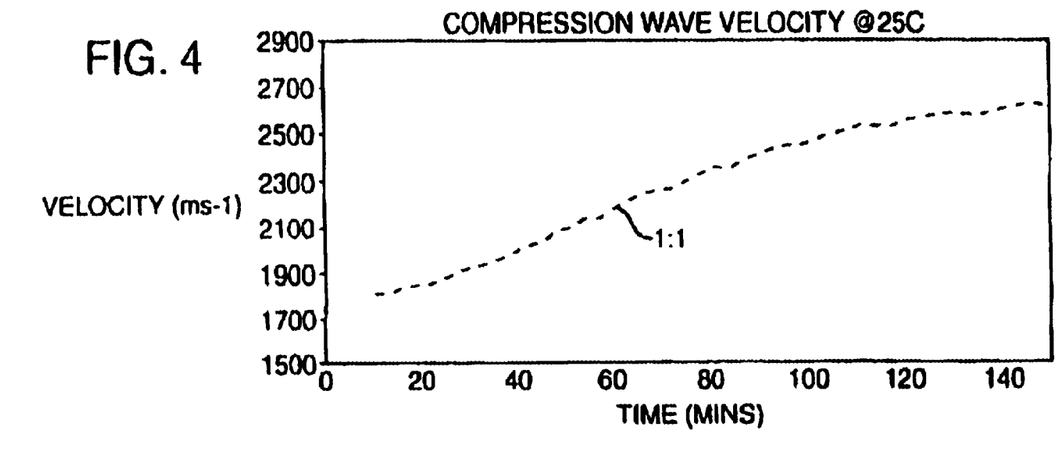
FIG. 4 is an ultrasound comparative graph showing compression wave velocity in the resin as a function of cure time, monitored by ultrasound methods.
Figure 5:
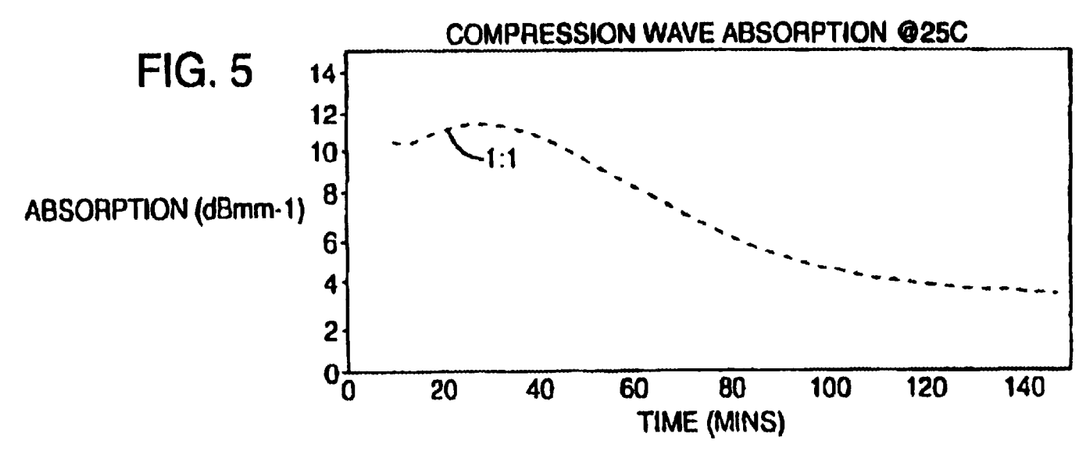
FIG. 5 is a comparative graph showing compression wave absorption as a function of cure time.
Figure 6:
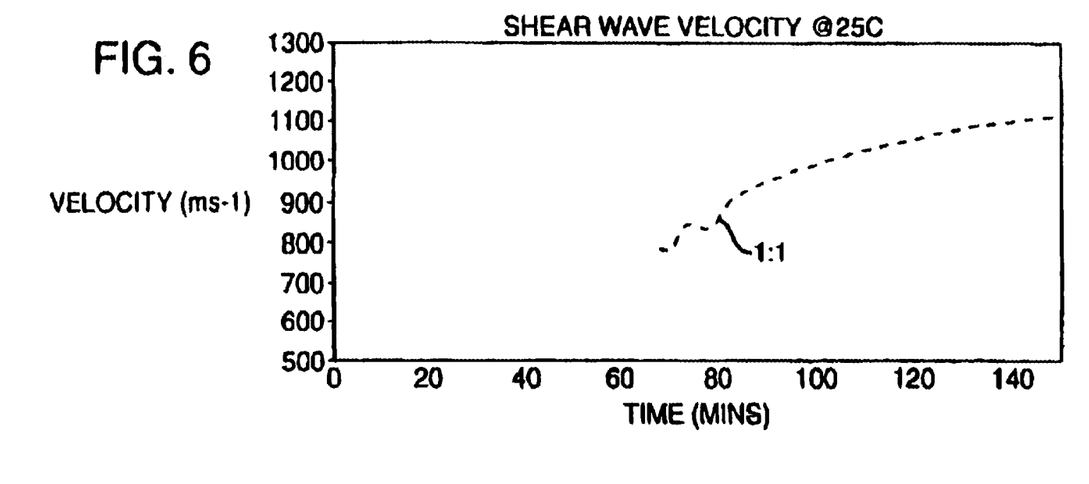
FIG. 6 is a comparative graph showing shear wave velocity as a function of cure time.
Figure 7:
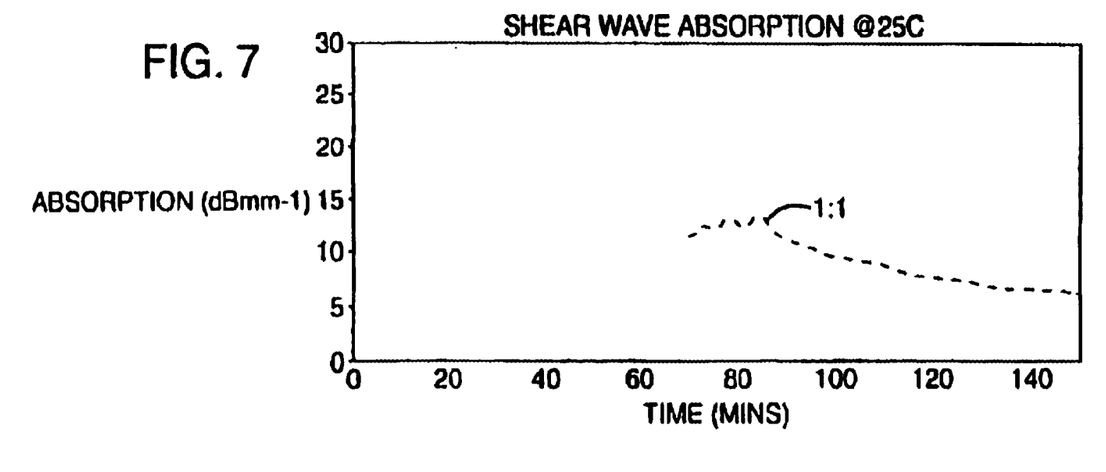
FIG. 7 is a comparative graph, which shows shear wave absorption as a function of cure time.

Stage 1, 0–27 minutes:

At an initial liquid phase, the resonant frequency of the bond is low and the signal amplitude high but changing slightly. This suggests that the resin is in an initial liquid phase with some reaction occurring producing slight changes in viscosity of the resin. It should be noted at this point that the transducers used in the experiment only measure movement in a vertical direction. The signal amplitude values associated with a bond containing uniform liquid resin are very much smaller than those associated with a void, due to the viscoelastic damping effects of the viscous resin.

During the same time period the NMR data indicates a high liquid content, high mobility of the hydrogen nuclei and low solid content. No shear waves (FIGS. 6 and 7) could be detected, confirming that the resin is in the liquid state. The Ultrasound compression wave velocity is low, indicating low compression modulus and, in addition, that attenuation first reduces slightly. This indicates small changes in the viscosity of the mix, which agrees with the slight changes in low frequency signal amplitude observed during this period.

Stage 2, 27–45 Minutes:

The resonant frequency of the bond begins to increase and signal amplitude reaches a minimum. This is indicative of the growth of long chain molecules in a liquid-like stage. Such materials are known to be sound absorbent, thus explaining the fall in signal amplitude as the increasingly absorbent resin damps the resonant vibrations. During the same time period the ultrasound compression wave absorption (FIGS. 4 and 5) reaches a maximum indicating that relaxations are taking place, which are indicative of large scale conformational changes.

Ultrasound compression wave velocity starts to increase at its maximum rate. NMR solid content (FIG. 8, solid line) is increasing rapidly and liquid content (dashed line) is falling rapidly. This of course indicates that the reaction rate is increasing. This is demonstrated by the increasing resonant frequency of the bond. Neither shear wave velocity or absorption can yet be detected indicating that the resin is still predominately liquid and that the gel point has not been reached.

Stage 3: 45–75 minutes.

The resonant signal amplitude begins to increase and the resonant frequency continues to increase to a maximum value. This indicates the initial cross-linking of the molecules to form a solid, the mechanical modulus of which increases as the cure proceeds. Gelation occurs during this phase, most likely at the time when the signal amplitude begins to increase. This is supported by ultrasonic results (FIG. 5) which show that over the same time period the compression wave absorption falls. Gelation is thought to occur on this falling edge of the absorption curve, though precisely where is a matter of debate.

Shear wave absorption and velocity become detectable at the latter end of this phase. Shear waves may only be supported by solid material and therefore gelation must occur prior to this point, i.e. prior to 70 minutes cure time.

The NMR data (FIG. 8) reveal that at the beginning of the phase the resin is changing rapidly from liquid to solid and that by the end of the phase the bulk of the reaction is over. Stage 4, 75–85 Minutes.

The resonant frequency remains constant at a maximum value. The signal amplitude reaches and maintains a maximum value. These results indicate that, to within the resolution of the current experimental set up, the reaction is over. This is supported by the NMR data, which show that very little further conversion from liquid to solid takes place after this stage.

However it can be seen from the ultrasound results that both shear and compression velocity continue to increase beyond this time. In fact these characteristics can continue to increase slightly until a cure time of 48 hours. This implies that the maxima seen in the low-resolution experiment are in fact indicative of green strength being achieved.

The foregoing shows that the low frequency method of the present invention is capable of resolving a number of key points in the curing of a resin, viz. the liquid phase, the growth of long chain molecules, the gel point of the resin, and the onset of green strength in the resin.

What is claimed is:

1. A method of monitoring the progress of solidification of a solidifying material, which method comprises
   (i) subjecting said solidifying material to a compression wave signal of relatively low frequency having a square wave format, said compression wave signal being adapted to induce resonant compression wave vibrations in said solidifying material, said resonant vibrations having a frequency higher than said compression wave signal; and,
   (ii) detecting and characterising at least one mode of said resonant compression wave vibrations induced in said solidifying material, thereby to indicate the progression of solidification.

2. A method as claimed in claim 1 wherein said compression wave signal has a frequency in the range of about 20 to 40 Hz.

3. A method as claimed in claim 1, wherein said solidifying material is selected from one or more of the group consisting of a thermosetting polymer, an epoxy resin and a thermoplastics resin.

4. A method as claimed in claim 1, wherein said solidifying material comprises a curable material.

5. A method as claimed in claim 4 wherein said curable material comprises a thermosetting polymer.

6. A method as claimed in claim 1, wherein said detecting and characterising step comprises monitoring the frequency and/or amplitude of said at least one mode with time.

7. A method as claimed in claim 1, wherein said detecting and characterising step comprises monitoring an increase in frequency of said at least one mode which is indicative of a decrease in the flexibility of the solidifying material as solidification progresses, and a signal amplitude which generally decreases to a minimum part way through solidification before increasing again as the solidification proceeds to completion.

8. Apparatus for monitoring the progress of solidification of a solidifying material, which apparatus comprises:
   (i) a transmitter that is adapted to transmit a compression wave signal to said solidifying material, said compression wave signal having a relatively low frequency and a square wave format and being adapted to induce resonant compression wave vibrations within said solidifying material having a frequency higher than said compression wave signal,
   (ii) a receiver that is adapted for detecting said resonant compression wave vibrations induced in said solidifying material, and
   (iii) analysing means for analysing the detected resonant compression wave vibrations, thereby to obtain an indication of the progress of solidification.

9. Apparatus as claimed in claim 8, wherein said transmitter is adapted to apply to said solidifying material a compression wave signal having a frequency in the range of about 20 to 40 Hz.

10. Apparatus as claimed in claim 8, wherein said solidifying material is selected from a one or more of the group consisting of a thermosetting polymer, an epoxy resin and a thermoplastics resin.

11. Apparatus as claimed in claim 8, wherein said solidifying material comprises a curable material.

12. Apparatus as claim in claim 11, wherein said curable material comprises a thermosetting material.

13. Apparatus as claimed in claim 8, wherein said analysing means are adapted to monitor the frequency and/or amplitude of said resonant compression wave vibrations with time.

14. Apparatus as claimed in claim 8, wherein said transmitter comprises a piezo-electric transducer.

15. Apparatus as claimed in claim 8, wherein said receiver and said transmitter are adapted to be spaced apart from one another in use, with each of said transmitter and said receiver contacting an exposed surface of a member, which member contacts said solidifying material, wherein said compression wave signal is transmitted through said member from said transmitter to said solidifying material, and said induced resonant compression wave vibrations in said solidifying material are transmitted through said member to said receiver.

16. Apparatus as claimed in claim 8, wherein the receiver comprises a piezo-electric transducer that is adapted to convert the resonant compression wave vibrations induced by the transmitter in the solidifying material into an electric signal.

17. Apparatus as claimed in claim 16, wherein said analysing means are configured to analyse the electric signal from the receiver to provide information about the progress of solidification of said solidifying material.

18. Apparatus as claimed in claim 17, wherein said analysing means comprise a database comprising data relating to the sound transmission characteristics of one or more solidifying materials, and said analysing means are configured to compare changes in said electric signal with corresponding data in said database.

19. Apparatus as claimed in claim 14, further comprising a pulser that is configured to drive said transmitter.

20. Apparatus as claimed in claim 19, wherein said analysing means comprise a digital storage adapter having first and second input channels and first and second outputs, a computer, and an oscilloscope, said pulser being connected to said first input channel, and said second input channel being connected to said receiver; said receiver being adapted to generated an electric signal corresponding to said detected resonant compression wave vibrations, said first output being connected to said oscilloscope to provide a visual signal indication, and said second output being connected to said computer, said computer being configured to store and process said electric signal to provide information about the solidification.

21. Apparatus as claimed in claim 8, wherein a single transducer acts as both a receiver and a transmitter.

22. Apparatus as claimed in claim 8, wherein said analysing means are adapted to monitor an increase in frequency of the induced resonant compression wave vibrations which is indicative of a decrease in the flexibility of the solidifying material, and a signal amplitude which generally decreases to a minimum part way through solidification before increasing again as solidification proceeds to completion.

23. A method as claimed in claim 1, wherein said at least one mode of said induced resonant compression wave vibrations has a frequency in the range of about 1–2 kHz.

24. Apparatus as claimed in claim 8, wherein said at least one mode of said induced resonant compression wave vibrations has a frequency in the range of about 1–2 kHz.

25. A method of monitoring the progress of solidification of a solidifying material, which method comprises:
(i) subjecting and solidifying material to a compression wave signal having a square wave format that is adapted to induce resonant compression wave vibrations in said solidifying material, said resonant compression wave vibrations having a frequency higher than said compression wave signal, said compression wave signal having a low frequency such that said induced resonant vibrations have a frequency in the order of kilohertz (kHz); and
(ii) detecting and characterising at least one mode of said resonant compression wave vibrations induced in said solidifying material, thereby to indicate the progression of solidification.

26. A method as claimed in claim 25, wherein said compression wave signal has a frequency in the range of about 20 to 40 Hz.

27. A method as claimed in claim 25, wherein said solidifying material is selected from one or more of the group consisting of a thermosetting polymer, an epoxy resin and a thermoplastics resin.

28. A method as claimed in claim 25, wherein said solidifying material comprises a curable material.

29. A method as claimed in claim 28, wherein said curable material comprises a thermosetting polymer.

30. A method as claimed in claim 25, wherein said detecting and characterising step comprises monitoring the frequency and/or amplitude of said at least one mode with time.

31. A method as claimed in claim 25, wherein said detecting and characterising step comprises monitoring an increase in frequency of said at least one mode which is indicative of a decrease in the flexibility of the solidifying material as solidification progresses, and a signal amplitude which generally decreases to a minimum part way through solidification before increasing again as the solidification proceeds to completion.

32. Apparatus for monitoring the progress of solidification of a solidifying material, which apparatus comprises:
(i) a transmitter that is adapted to transmit a compression wave signal to said solidifying material, which compression wave signal is adapted to induce resonant compression wave vibrations in said solidifying material having a frequency higher than said compression wave signal, said compression wave signal having a low frequency such that said induced resonant vibrations have a frequency in the order of kilohertz,
(ii) a receiver that is adapted for detecting said resonant compression wave vibrations induced in solidifying material, and
(iii) analysing means for analysing the detected resonant compression wave vibrations, thereby to obtain an indication of the progress of solidification.

33. Apparatus as claimed in claim 32, wherein said transmitter is adapted to apply to said solidifying material a compression wave signal having a frequency in the range of about 20 to 40 Hz.

34. Apparatus as claimed in claim 32, wherein said solidifying material is selected from one or more of the group consisting of a thermosetting polymer, an epoxy resin and a thermoplastics resin.

35. Apparatus as claimed in claim 32, wherein said solidifying material comprises a curable material.

36. Apparatus as claimed in claim 35, wherein said curable material comprises a thermosetting polymer.

37. Apparatus as claimed in claim 32, wherein said analysing means are adapted to monitor the frequency and/or amplitude of said resonant compression wave vibrations with time.

38. Apparatus as claimed in claim 32, wherein in said transmitter comprises a piezo-electric transducer.

39. Apparatus as claimed in claim 32, wherein said receiver and said transmitter are adapted to be spaced apart from one another in use, with each of said transmitter and said receiver contacting an exposed surface of a member, which member contacts said solidifying material, wherein said compression wave signal is transmitted through said member from said transmitter to said solidifying material, and said induced resonant compression wave vibrations in said solidifying material are transmitted through said member to said receiver.

40. Apparatus as claimed in claim 32, wherein the receiver comprises a piezo-electric transducer that is adapted to convert the resonant compression wave vibrations induced by the transmitter in the solidifying material into an electric signal.

41. Apparatus as claimed in claim 40, wherein said analysing means are configured to analyse the electric signal from the receiver to provide information about the progress of solidification of said solidifying material.

42. Apparatus as claimed in claim 41, wherein said analysing means comprise a database comprising data relating to the sound transmission characteristics of one or more solidifying materials, and said analysing means are configured to compare changes in said electric signal with corresponding data in said data base.

43. Apparatus as claimed in claim 38, further comprising a pulser that is configured to drive said transmitter.

44. Apparatus as claimed in claim 43, wherein said analysing means comprise a digital storage adapter having first and second input channels and first and second outputs, a computer, and an oscilloscope, said pulser being connected to said first input channel, and said second input channel being connected to said receiver; said receiver being adapted to generate an electric signal corresponding to said detected resonant compression wave vibrations, said first output being connected to said oscilloscope to provide a visual signal indication and said second output being connected to said computer, said computer being configured to store and process said electric signal to provide information about the solidification.

45. Apparatus as claimed in claim 32, wherein a single transducer acts as both a receiver and transmitter.

46. Apparatus as claimed in claim 32, wherein said analysing means are adapted to monitor an increase in frequency of the induced resonant compression wave vibrations which is indicative of a decrease in the flexibility of the solidifying material, and a signal amplitude which generally decreases to a minimum part way through solidification before increasing again as solidification proceeds to completion.

47. A method as claimed in claim 25, wherein said at least one mode of said induced resonant compression wave vibrations has a frequency in the range of about 1–2 kHz.

48. Apparatus as claimed in claim 32, wherein said at least one mode of said induced resonant compression wave vibrations has a frequency in the range of about 1–2 kHz.

* * * * *